United States Patent [19]

Hardwick

[11] Patent Number: 5,025,777
[45] Date of Patent: Jun. 25, 1991

[54] CHEMICALLY HEATED BLANKET

[75] Inventor: Eugene R. Hardwick, Encino, Calif.

[73] Assignee: Karen Worchell, Studio City, Calif.

[21] Appl. No.: 482,333

[22] Filed: Feb. 20, 1990

Related U.S. Application Data

[63] Continuation-in-part of Ser. No. 433,697, Nov. 9, 1989.

[51] Int. Cl.$^5$ .............................................. F24J 1/00
[52] U.S. Cl. .................................... 126/263; 126/204; 128/403
[58] Field of Search ............... 126/263, 204, 205, 206, 126/207, 269, 400; 128/254, 403, 399, 402; 165/46

[56]  References Cited

U.S. PATENT DOCUMENTS

| | | | |
|---|---|---|---|
| 4,516,564 | 5/1985 | Koiso et al. | 126/263 |
| 4,572,188 | 2/1986 | Augustine et al. | 126/204 |
| 4,664,674 | 5/1987 | Oftedal et al. | 126/263 |
| 4,756,299 | 7/1988 | Podella | 126/263 |

Primary Examiner—James C. Yeung
Attorney, Agent, or Firm—Irell & Manella

[57] ABSTRACT

The present invention relates to a chemical warmer which comprises an air supply device, a first and a second panel peripherally fastened to each other to form an envelope to contain a chemical thermogenic material. The first panel is configured to include an air-impermeable top layer, an air-permeable middle layer with a plurality of air holes therethrough and an air-permeable inner layer with many micropores therethrough, the top and middle layers being partially welded to each other in such a way that a plurality of air distribution passages and gas exhaust passages are formed for uniformly distributing air inside the panel and extracting exhaust gases/air to a gas exit which is connected to size-adjustable wastegate device. The second panel includes at least an air-impermeable layer. The air supply device is either hand-operated or electronically powered. The present invention further discloses an exothermic material mat which can keep the thermogenic material in place throughout the mat.

5 Claims, 3 Drawing Sheets

CHEMICALLY HEATED BLANKET

BACKGROUND OF THE INVENTION

This is a continuation in part of application Ser. No. 07/433,697 filed Nov. 9, 1989, in the name of E. Russell Hardwick and assigned to the assignee of the present invention.

The present invention relates to a chemical warmer, and especially to a chemically heated blanket.

A chemical warmer has many known advantages and uses since no flame is produced. It is widely used in hospitals, homes and outdoors for applying heat to a human body or other objects. Consequently, various types of such devices are known in the art. Many improvements have been made in the chemical exothermic materials used in the chemical warmers, one useful type uses air for activating and maintaining the thermogenic chemical reactions in the chemical warmer. In order to introduce air into a chemical warmer, the conventional chemical warmers usually utilize an air-permeable inner bag which is enclosed in an air-impermeable outer bag, or covered by an air-impermeable film or the like. The inner bag may have one or more air-permeable layers which are provided with many air holes or micropores. Initiation of the heating process occurs when the inner bag is exposed to air. Numerous patents have been granted for improvements in such chemical warmers such as the following U.S. patents: U.S. Pat. No. 4,756,299 issued on July 12, 1988 to Car W. Podella, U.S. Pat. No. 4,268,272 issued on May 19, 1981 to Miyako Taura, U.S. Pat. No. 3,976,049 issued on Aug. 24, 1976 to Iwao Yamashita et al, and U.S. Pat. No. 3,301,250 issued on Jan. 31, 1967 to Ernest C. Glasser.

One of the important factors which affects the thermogenic reaction is the amount of air supply per time unit. Due to the structures of the previous chemical warmers, the rate of air supply is adjustable only to a very imprecise degree. As a result, the heat output from the warmer cannot be effectively controlled. In other words, the temperature of the chemical warmer is not controllable. Moreover, in most prior art, the air cannot be efficiently and uniformly supplied to all parts of the thermogenic material, causing hot and cold spots. Furthermore, the thermogenic reaction or heating process is not easily stopped when desired as to the prior art. Normally, the conventional chemical warmer must be taken away from the heated body and put back into an air impermeable bag or resealed by a film in order to stop the production of heat.

Another important factor which affects the uniform heat output throughout the warmer or blanket is the manner of containing the exothermic materials. In conventional warmers, the powdered exothermic material or composition is merely placed loose between two loose covers which form a bag or envelope. This structure has been shown by the U.S. Pat. Nos. 4,268,272, 3,976,049, 4,516,564, 4,756,299. With this configuration, the powdered exothermic material tends to gravitate all to one place, like a bag of dirt, and cannot be kept in place. Accordingly, the heat cannot be evenly distributed throughout the heated area, especially in the case of a big warmer, such as a blanket.

All of these shortcomings associated with the conventional chemical warmers limit their applications or areas of use.

The present invention provides a novel chemical warmer which overcomes the limitations and shortcomings of the prior art devices.

OBJECT OF THE INVENTION

One object of the present invention is to provide a chemical warmer which can control the heat output of the chemical warmer by controlling the supply of air.

Another object of the present invention is to provide a chemical warmer that can efficiently and uniformly distribute air to all parts of the warmer.

Still another object of the present invention is to provide a chemical warmer in which the production of heat can be easily stopped without removing the chemical warmer from the context of its application.

A further object of the present invention is to provide a chemically heated blanket that has the above-mentioned advantages and can be used in hospitals, homes, automobiles or outdoors.

Another object of the present invention is to provide an exothermic material mat which can uniformly hold the exothermic material in place and is permeable to air.

These and other important objects of the present invention will be apparent from the detailed description provided hereafter.

SUMMARY OF THE INVENTION

This invention is an improved chemical warmer or chemically heated blanket of the air-activated type, which can supply heat to the human body or other objects. The chemically heated blanket comprises an air supply device for introducing atmospheric air into the blanket, a gas exhaust exit for extracting the exhaustion gases, and first and second panels forming an envelope which contains the chemical exothermic material.

The first panel, functioning as an air distribution and gas exhaust system, includes a top layer of air-impermeable material, a middle layer of air-permeable material with a plurality of air holes therethrough and an inner layer of air-permeable material having many air micropores, the top and middle layers being partly welded to each other in such a way that a plurality of air passages and gas exhaust passages are formed between them for uniformly distributing air from the air supply device to inside the panel and transferring exhaust gases to the gas exhaust exit. The second panel is provided with at least a layer of air-impermeable material. The air supply device which is connected to the air passages by means of an air entrance, can be either a hand-operated, an electrically powered type, or any other means of introducing air. The gas exhaust exit is provided with a wastegate, the size of which is adjustable.

In another embodiment, the air distribution system and the gas exhaust system are separately structured on the first and second panels.

The present invention further discloses an exothermic material mat which can be used in a chemical warmer, including the conventional chemical warmers. The exothermic material mat includes an exothermic material containing panel which has a plurality of uniformly distributed spaces for holding the powdered exothermic material in place so that heat can be produced evenly throughout the surface of the chemical warmer.

Some preferred embodiments and features of the present invention will be described hereafter by referring to the attached drawings.

DESCRIPTION OF THE DRAWINGS

FIG. 7A is a cross-sectional view of such a mat in which only one of the membranes has a plurality of uniformly distributed hollows thereon for containing the chemical material. FIG. 7B is a cross-sectional view of such a mat with the two membranes having uniformly distributed hollows thereon.

DETAILED DESCRIPTION OF THE INVENTION

Figure 1:
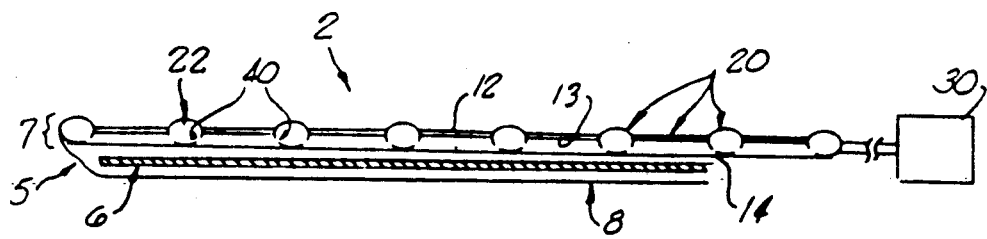
FIG. 1 is a cross-sectional view of an embodiment of the chemically heated blanket of the present invention.
Figure 2:
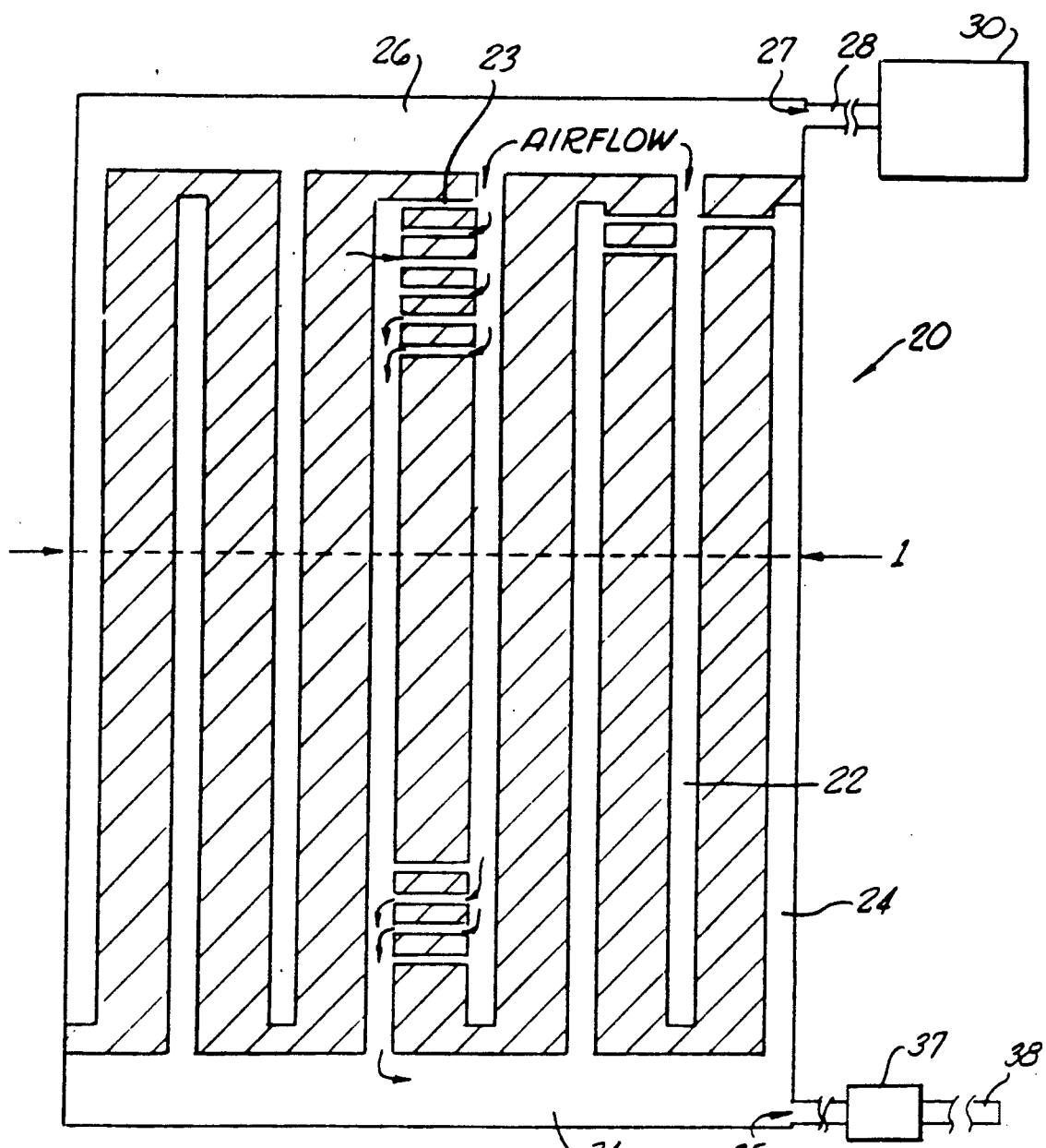
FIG. 2 is a cross-sectional plan view of an arrangement of the air passages and gas exhaust passages of the embodiment shown in FIG. 1.

Turning in detail to the drawings, FIGS. 1 and 2 show a preferred embodiment of a chemically heated blanket 2 of the present invention which has an air supply device 30 and an air distribution and gas exhaust system 20.

The thermogenic chemical material used in the present invention can be any kind of air-oxidizable thermogenic materials known in the prior art, such as the materials described in U.S. Pat. No. 4,093,424.

The chemically heated blanket 2 includes an envelope 5 which is formed by two panels 7 and 8, whereby the exothermic chemical material 6 is accommodated therein. The panel 8 is constructed from a layer of air-impermeable material. The other panel 7 has a laminated configuration which preferably consists of an air-impermeable top layer 12, an air-permeable middle layer 13 with a plurality of air holes 40 therethrough and an air-permeable inner layer 14 having many micropores therethrough or made of an air permeable material. As an example, these air holes 40 may be 1 mm diameter holes spaced on 1 cm centers, although the size and spacing of the holes will depend on the type of thermogenic material and the intended conditions of use. The top layer 12 and the middle layer 13 are partially united to each other in such a way that a plurality of air passages and gas exhaust passages are provided. Since the pressure along the passages will decrease progressively, the number of the air holes on the middle layer 13 can be arranged to increase progressively from the input end to the remote end of the passages so that the air can be uniformly distributed. Gas exhaust, as used herein, refers to air exiting from the distribution system together with by products (to the extent they exist) from the thermogenic chemical reaction. The two panels can be made of thermoplastic materials, heat-welded into the desired form and then incorporated into the blanket.

The arrangement of the passages is shown in FIG. 2, and includes a plurality of longitudinal air passages 22 and longitudinal gas exhaust passages 24, and many transverse sub-passages 23 uniformly arranged between the longitudinal air passages 22 and the longitudinal gas exhaust passages 24 at equal intervals to each other. (Only a few of the transverse sub-passages are schematically shown in FIG. 2.) It should be understood that the arrangement of the passages shown in FIG. 2 is only an example. Some other arrangements may also be chosen as long as the air distribution and gas exhaust system can introduce fresh air and extract exhausted gases uniformly across all parts of the blanket. For example, the transverse sub-passages may not be necessarily needed. All the longitudinal air passages are connected to an air entrance chamber 26 extending across the head of the blanket like a section of an air mattress and acting as a buffer against pulsing of the air supply. The entrance chamber 26 can store one or more minutes of air supply and forms the initial distribution mechanism, while all the longitudinal gas exhaust passages are connected to an outlet chamber 34 extending across the opposite head of the blanket with a diameter somewhat smaller than the entrance chamber.

Figure 5:
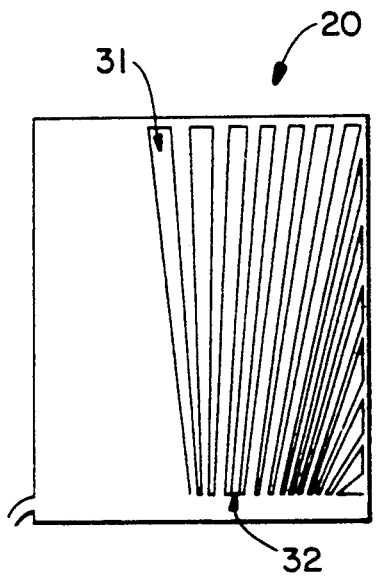
FIG. 5 is a plan view of another arrangement of the air distribution system of the present invention in which only a part of air passages are schematically shown.

Another example of the arrangement of the air distribution system 20 is shown in FIG. 5. The air passages may be structured in a fan-shaped channel 31; that is, the diameter of the air passages varies successively in cross-section along the channel 31, being small at the input end 32 (where the pressure is highest) and larger as it gets further from the supply.

As an alternative, the air distribution system can also be formed by using a plurality of air-permeable small tubes, such as vinyl tubes, or fabricated in such a way that the channel will exist even under no air pressure.

Air is supplied externally through a tube 28 leading to an air entrance 27 of the air entrance chamber 26. Air supply to the tube 28 is from an air supply device 30 which can be a small air compressor or air pump powered by line current, batteries or other means. A small compressor may be incorporated into the blanket itself, with electric power supplied by batteries. Various types of compressors can be used for this purpose, for example, the piston type, diaphragm type, gear type or any device that can deliver air at a suitable pressure. Air may also be delivered by means of a hand-operated air supply device, such as a squeeze bulb, a bellows, an accordion device or other similar means. The air pressure is in range of about 5 to 15 cm of mercury at a rate of 1 or more liters/minute. But it should be understood that the air pressure of the air supply is determined depending on the size of the blanket, the type of thermogenic material used and the temperature needed. It is calculated that an air flow of 1 L/min would be sufficient, given standard thermogenics, to produce a heat in excess of that given by a standard electrically heated twin-bed blanket operated at a moderate rate at temperatures somewhat below room temperature.

In order to avoid overly hot temperatures, particularly while the blanket covers an unconscious person, a temperature controlled valve may be utilized in the air supply tube (not shown in the drawings). Such a valve may be bistable, so that it allows either an unrestricted flow at low temperatures or essentially no flow above a certain temperature, or a valve with a continuously variable position with respect to temperature. In another approach, a temperature-controlled electronically operated air pump system may be used, which may include a temperature sensor and a control circuit.

The exhaust gases exit from a gas exit 35 leading from the outlet chamber 34. There is provided a wastegate device 37 which is connected to the exit 35 and includes a restricted gate of either fixed or adjustable size for the purpose of assuring an optimum pressure in the blanket system. The wastegate device can be any suitable valve or the like, including a simple cam roller acting in combination with a deformable plastic tube. An outflow tube 38 can be provided for leading the exhaust gases away from the blanket to diminish the concentration of exhaust gases near the person lying on the blanket.

During the thermogenic operation, air is supplied by means of the air supply device 30 into the air entrance chamber 26, then air is delivered into a series of air passages 22 under pressure so that a second stage of air distribution occurs. Air continues flowing into sub passages 23 in a matrix pattern and final air distribution occurs. Passing through the holes on the layer 13 of the air distribution system, air reaches the final air permeable layer 14 in a uniform manner. Finally, air passes through the final layer 14 and activates the thermogenic reaction. Any gases produced in the reaction together with excess air will exit through the gas exhaust passages 24 under the difference in pressures between the gas exhaust system and reaction space. Control of the heat output of the blanket is achieved simply by controlling the rate of input airflow. If the airflow is stopped completely, the blanket could be shut off by terminating the air necessary to react with the thermogenic materials.

Figure 3:
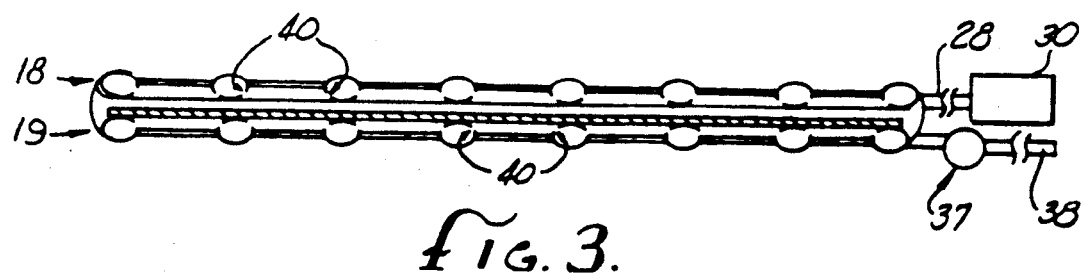
FIG. 3 is a cross-sectional view of another embodiment of the chemically heated blanket of the present invention.
Figure 4:
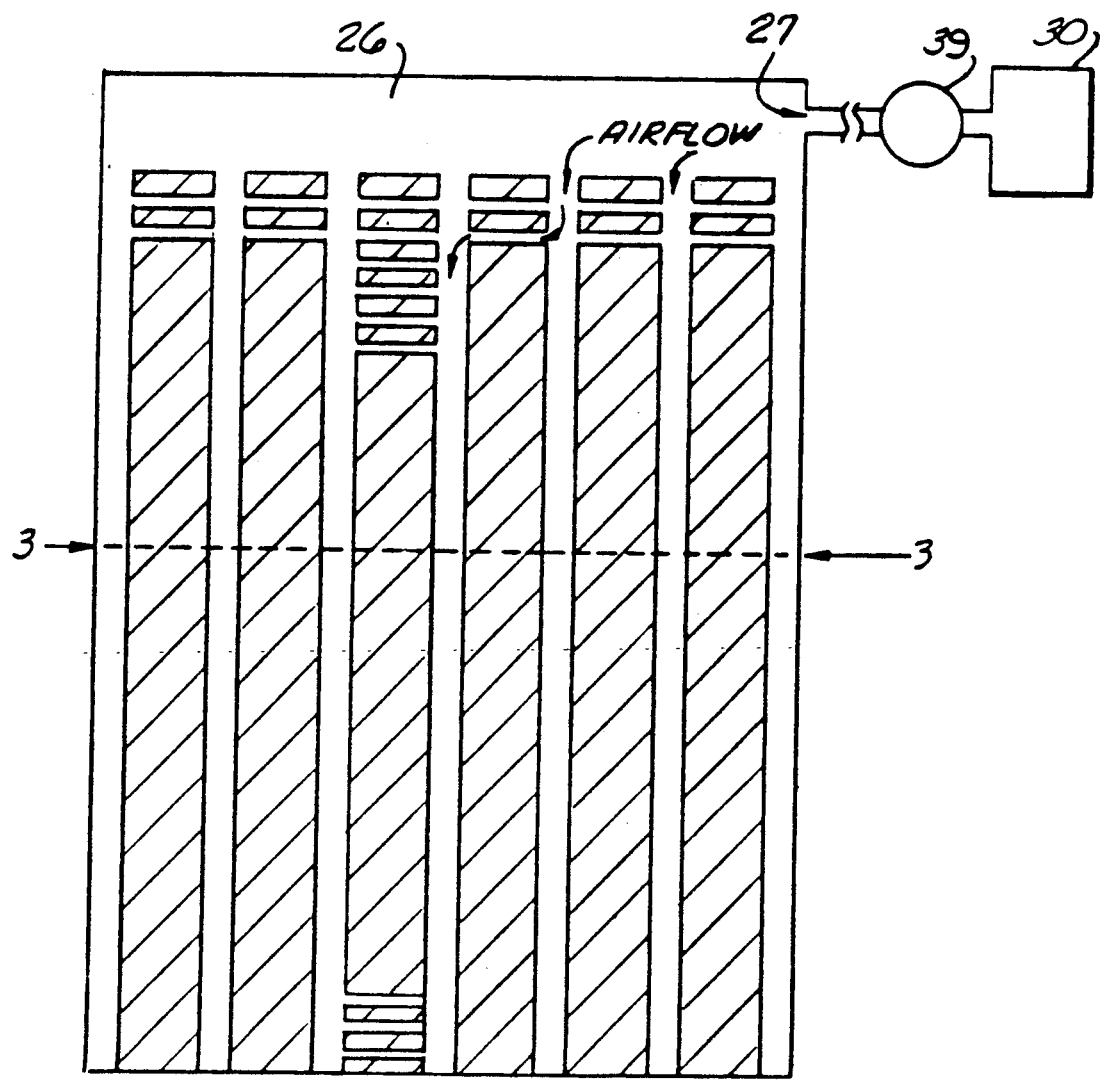
FIG. 4 is a cross-sectional plan view of the arrangement of the air passages of the embodiment shown in FIG. 3.

Referring now to FIGS. 3 and 4, there is shown another embodiment of the chemically heated blanket which has an air distribution system 18 on one panel of the blanket, and a similarly structured gas/air exhaust system 19 on the other panel. The outlet chamber, in this case, can be at the same end as the entrance chamber 26, allowing better access to wastegate control. In use, the exhaust surface may be the surface next to the human body so as to help distribute heat evenly, diminishing the presence or effect of hot spots. In this embodiment, it is necessary that air be able to pass through the thermogenic material, which can be configured to make this possible.

In order to obtain a calibrated heat output, particularly when the blanket is used in hospitals, an air flowmeter 39 or a pressure gauge may be employed on the air input line or on the gas output line.

Figures 6B, 6C:
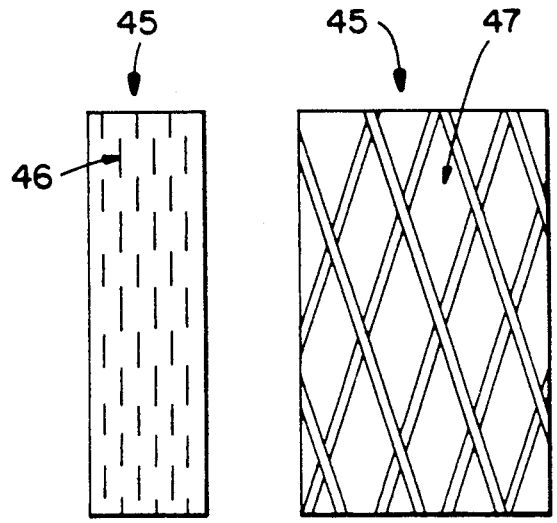
FIGS. 6B and 6C show a process of making a screen with diamond-shaped holes therethrough.
Figure 6A:
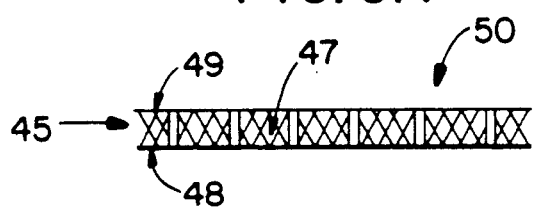
FIG. 6A is a cross-sectional view of an embodiment of the thermogenic material mat of the present inventions which can keep the exothermic material uniformly in place throughout the mat.

FIG. 6A is a cross-sectional view of a thermogenic material mat 50, which can keep the thermogenic material in place and be disposed in the air-permeable envelope of a chemical warmer. The thermogenic material mat 50 includes a screen or net 45 with many uniformly distributed small holes 47 for containing the powdered thermogenic material, two air-permeable membranes 48 and 49 having a plurality of uniformly distributed micropores therethrough and fastened respectively on the two surfaces of the screen 45. Such screen 45 can be manufactured by creating appropriately located slits 46 in a sheet of plastic foam 45, as shown in FIG. 6B, such as a sheet of approximately one-eighth inch thick polyethylene. The sheet is then expanded to form a diamond-shaped pattern of holes 47, as shown in FIG. 6C. The air-permeable membranes 48 and 49 may be made of a thin polyethylene sheet perforated with microscopic holes. During manufacture, the membrane is first welded or cemented onto the expanded screen so as to form many cells. The welding can be accomplished by placing the screen on a flat surface, covering it with the membrane, and pressing a hot, teflon-coated roller over it. After the cells are filled with the powdered thermogenic material, the second membrane is welded or cemented onto the other surface of the screen. The perforation may first be non-permeable and perforated after the welding is done. Of course, the portion of the process involving the reactive substance must be carried out in the absence of air. The screen may also be formed by uniformly punching tiny holes in a layer of suitable material, and the air-permeable membrane can be an air-permeable and sticky film, such as the product made by 3M called micropore tape, which can be simply taped onto the surfaces of the screen. Any array of holes of any shape and of a wide range of sizes may constitute the cells. The main purpose is to trap the thermogenic material uniformly in the screen so that it cannot migrate and can provide a uniform heat output throughout the screen.

Figure 7A:
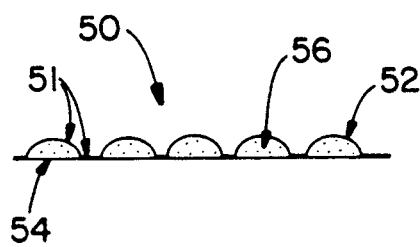
FIGS. 7A and 7B show another embodiment of the exothermic material mat of the present invention which is formed by two air-permeable membranes.
Figure 7B:
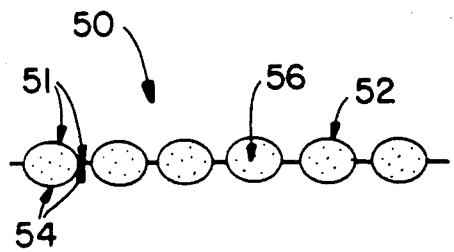

FIGS. 7A and 7B show another preferred embodiment of the thermogenic material mat 50. The mat 50 is formed by two air-permeable membranes 51 and 54 which are welded or cemented to each other. In this embodiment, at least one of the membranes includes a plurality of uniformly distributed and depressed small hollows 52, as shown by FIGS. 7A and 7B. The thermogenic material 56 is held in the cells between the two air-permeable membranes 51 and 54.

In the case that both membranes 51 and 54 have hollows as shown in FIG. 7B, the hollows on the two membranes match each other so that large cells can be provided and easily manufactured.

In a simplified alternative, an absorbent substrate is adopted, into which the thermogenic material can be uniformly distributed. The absorbent substance may be absorbent fiber, such as a thin layer of cotton or a similar fibrous material, permeated with the active material, or a layer of filamentary fine steel wool, the absorbent substrate being anchored by the quilting welds passing through it.

While the preferred application of the present invention has been shown and described, it should be apparent to those skilled in the art that many more modifications are possible without departing from the invention concept herein described. It is intended to cover in the appended claims all such modifications as fall within the true spirit and scope of the invention.

What is claimed is:

1. A chemical warmer, comprising:
   an envelope having a first panel means and a second panel means peripherally connected to said first panel means to form said envelope,
   an air introduction means for introducing air into said envelope,
   a gas exhaust means for exhausting exhaust gas out of said envelope,
   a powdered or granular thermogenic material or mixture, and
   a thermogenic material mat disposed in said envelope for holding said thermogenic material therein in place, said mat including a first sheet of air-permeable material having a plurality of depressed small hollows, and a second sheet of material welded or cemented onto said first sheet of material to form a plurality of distributed cells therebetween for holding said thermogenic material in place.

2. A chemical warmer claimed in claim 1, wherein said second sheet of material is also made of air-permeable material.

3. A chemical warmer claimed in claim 1, wherein said first sheet of air-permeable material and said second sheet of material are made of a plastic material.

4. A chemical warmer claimed in claim 2, wherein said first and second sheet of air-permeable material includes a plurality of uniformly distributed micropores therethrough.

5. A thermogenic material mat claimed in claim 1, wherein said second sheet of material also includes a plurality of evenly distributed and small depressed hollows matching with the hollows on said first sheet of air-permeable material.

* * * * *